US008758755B2

(12) United States Patent
Harris et al.

(10) Patent No.: US 8,758,755 B2
(45) Date of Patent: *Jun. 24, 2014

(54) STEM CELL FUSION MODEL OF CARCINOGENESIS

(75) Inventors: David T. Harris, Tucson, AZ (US); Tom C. Tsang, Tucson, AZ (US); Xianghui He, Tianjin (CN); Brian L. Pipes, Tucson, AZ (US); Linda C. Meade-Tollin, Tucson, AZ (US)

(73) Assignee: Arizona Board of Regents on behalf of the University of Arizona, Tucson, AZ (US)

( * ) Notice: Subject to any disclaimer, the term of this patent is extended or adjusted under 35 U.S.C. 154(b) by 168 days.

This patent is subject to a terminal disclaimer.

(21) Appl. No.: 13/448,112

(22) Filed: Apr. 16, 2012

(65) Prior Publication Data

US 2012/0201808 A1 Aug. 9, 2012

Related U.S. Application Data

(62) Division of application No. 12/064,745, filed as application No. PCT/US2006/033366 on Aug. 25, 2006, now Pat. No. 8,158,126.

(60) Provisional application No. 60/711,249, filed on Aug. 25, 2006.

(51) Int. Cl.
*A61K 39/395* (2006.01)

(52) U.S. Cl.
USPC .................................. 424/141.1; 424/130.1

(58) Field of Classification Search
USPC ........................................ 424/141.1, 130.1
See application file for complete search history.

(56) References Cited

U.S. PATENT DOCUMENTS

| 5,558,852 | A | 9/1996 | Bigner et al. | |
|---|---|---|---|---|
| 6,007,816 | A | 12/1999 | St. John et al. | |
| 6,007,819 | A | 12/1999 | Taub et al. | |
| 8,158,126 | B2 * | 4/2012 | Harris et al. | 424/141.1 |
| 2007/0021378 | A1 * | 1/2007 | Varki et al. | 514/56 |

FOREIGN PATENT DOCUMENTS

| WO | WO9007321 | 7/1990 |
|---|---|---|
| WO | WO2004093646 | 11/2004 |

OTHER PUBLICATIONS

Laubli et al. (2006) Canc. Res., vol. 66, 1536-1542.*
St. John et al. (1986) Science, vol. 231 (4740), 845-850.*
Vogel et al. (2002) J. Clin. Oncol., vol. 20, 719-726.*
Qian et al. (2001) PNAS, vol. 98(7), 3976-398.*
Abcam Online Catalog (the Anti-Ubiquitin antibody portion of the Abcam Online Catalog and the Abcam support page of Ab411), printed on Mar. 29, 2010 and Jun. 13, 2012.*
http://www.abcam.com/ubiquitin-antibody-10c2-2-ab411.html, pp. 1-7.*
Bowen B R et al: "The MEL 14 Antibody Binds to the Lectin Domain of the Murine Peripheral Lymph Node Homing Receptor", The Journal of Cell Biology, Rockefeller University Press, US, vol. 110, No. 1, Jan. 1, 1990, pp. 147-153, XP000618239.
Chen et al., "Unveiling the Mechanisms of Cell-Cell Fusion", Science, Apr. 15, 2005, vol. 308, pp. 369-373.
Clarke et al., Stem Cells and Cancer: Two Faces of Eve, Cell, vol. 124, pp. 1111-1115.
Cokgor et al., Long Term Response in a Patient with Neoplastic Meningitis Scondary to Melanoma Treated with 1311-Radiolabeled Antichondroitin Proteoglycan Sulfate Mel-14 (ab')2, A Case Study, pp. 1809-1813, 2001 American Cancer Society.
Gallatin W M et al. "A cell-surface molecule involved in organ-specific homing of lymphocytes", Nature Jul. 7-13, 1983 LNKD-PUBMED:6866086, vol. 304, No. 5921, Jul. 7, 1983, pp. 30-34, XP002650350.
Geho et al., "Physiological Mechanisms of Tumor-Cell Invasion and Migration" Physiology, Jun. 2005, vol. 20, pp. 194-200.
He et al. "A Stem Cell Fusion Model of Carcinogenesis" Oct. 25, 2005, Journal of Experimental Therapeutics and Oncology, Rapid Science Publishes, London, GB, vol. 5, No. 2.
Lal et al., Mutant Epidermal Growth Factor Receptor Up-Regulates Molecular Effectors of Tumor Invasion, Cancer Res. Jun. 15, 2002, vol. 62, pp. 3335-3339.
Larizza L et al., "Suggestive evidence that the highly metastatic variant ESb of the T-cell lymphoma Eb is derived from spontaneous fusion with a host macrophase", International Journal of Cancer, Journal International DU Cancer Nov. 15, 1984, vol. 34, No. 5, Nov. 15, 1984, pp. 699-707, XP002507584.
Terada et al. "Bone Marrow Cells Adopt the Phenotype of Other Cells by Spontaneous Cell Fusion," Nature, Apr. 4, 2002, vol. 416, No. 6880.

* cited by examiner

*Primary Examiner* — Anne Marie S Wehbe
(74) *Attorney, Agent, or Firm* — Quarles & Brady LLP; Gavin J. Milczarek-Desai

(57) ABSTRACT

Methods for modeling cancer cell migration, screening drugs for effects on tumor cell migration, and detecting the potential for tumor cell migration relating to the fusion of a bone marrow derived stem cell with a genetically altered cell. Antibodies against ubiquitin are shown to inhibit tumor cell migration.

6 Claims, 1 Drawing Sheet

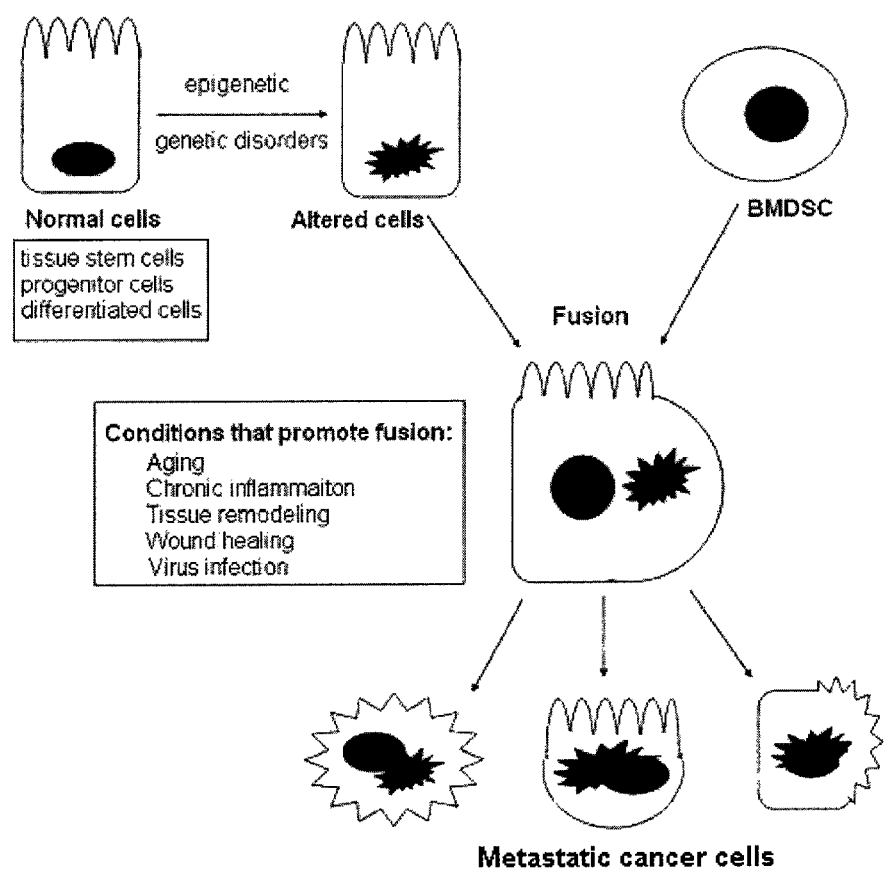

STEM CELL FUSION MODEL OF CARCINOGENESIS

CROSS REFERENCE TO RELATED APPLICATIONS

This application is a divisional application and claims the benefit of priority to PCT/US2006/033366, filed on Aug, 25, 2006, and to U.S. Ser. No. 12/064,745, now U.S. Pat. No. 8,158,126filed on Jul. 31, 2008, the entire contents of all of which are incorporated by reference.

BACKGROUND OF THE INVENTION

1. Field of the Invention

The invention relates to a cell system and method for modeling, screening drugs against, and inhibiting migration of cancer cells.

2. Description of the Related Art

Cancer has been difficult to treat because of tissue heterogeneity and gene instability. As a human disease, cancer was described as early as 1600 B.C. in ancient Egyptian writings. Hippocrates, the ancient Greek physician, recognized the difference between benign and malignant tumors and named malignant tumors "carcinos." Cancer is currently the second-leading cause of death in developed countries.

Tremendous knowledge of cancer has been accumulated since United States President Richard Nixon declared a "war on cancer" in the 1970s. Many hypotheses of cancer development have been proposed in the last two centuries. Early hypothesis included the irritation hypothesis, embryonal hypothesis and parasitic hypothesis. Later, with the establishment of experimental oncology, chemical carcinogens were identified. Dozens of oncogenes and tumor suppressor genes were discovered through molecular analysis of human and experimental animal tumors. These studies resulted in establishment of the gene mutation hypothesis, which has been dominant over the last three decades.

Despite its intrinsic elegance, the current gene mutation hypothesis has failed to explain many important features of cancer. Indeed, the limitations of the gene mutation hypothesis have been thoroughly addressed by many researchers.

Recently, the "stem cell theory of carcinogenesis" has gained momentum with insights gained from stem cell research and the discovery of "cancer stem cells." The stem cell theory of carcinogenesis suggests that stem cells accumulate genetic mutations and become malignant cells. However, since it is still totally dependent on the gene mutation hypothesis, the stem cell theory cannot fully address what causes the distinctive features of cancer, such as invasion and metastasis.

Mutations are rare events. Mathematical models suggest that a more frequent event is required for malignant transformation. Genomic instability was proposed as the enabling characteristic of the hallmarks of cancer. As the phenotype of genomic instability, aneuploidy has been observed in nearly all solid human cancers and is difficult to explain with gene mutation hypothesis. It has been proposed that aneuploidy accounts for cancer as an autonomous mutator, but the mechanism underlying aneuploidy remains unclear.

Hence, despite the substantial progress that has been made, the origin of cancer remains enigmatic. Because current models of carcinogenesis based on the gene mutation hypothesis have limitations in explaining many aspects of cancer, a new model of multistage carcinogenesis has been put forward by the inventors in which it is proposed that cancer development involves gene mutations and cell fusions. Specifically, cancer can result from a fusion between an "altered" pre-malignant cell and a bone marrow-derived stem cell (BMDSC). "Aneuploidy," which is a hallmark of malignancy, is a direct consequence of this cell fusion. The "stem cell fusion" model explains the remarkable similarities between malignant cells and BMDSC. This model also explains why non-mutagens can be carcinogens, and why non-mutagenic processes, such as wound healing and chronic inflammation, can promote malignant transformation.

SUMMARY OF THE INVENTION

In one embodiment of the invention, a method for modeling cancer cell migration is disclosed. The method preferably includes providing a bone marrow derived stem cell, providing a genetically altered cell, fusing the bone marrow derived stem cell with the genetically altered cell, thereby creating a fused cell; and measuring an indicator of migration for the fused cell. Alternatively, instead of fusing the two types of cells directly, one may obtain or culture the fused cell from a previous fusion of the bone marrow derived stem cell with the genetically altered cell.

In another embodiment of the invention, a method for screening an effect of a biological or chemical agent on tumor cell migration is described. The method includes providing a fused cell derived from a fusion of a bone marrow derived stem cell with a genetically altered cell, contacting the fused cell with a biological or chemical agent, and determining whether tumor cell migration is promoted, inhibited, or unchanged.

In yet another embodiment of the invention, a method for inhibiting tumor cell migration is described and includes comprising contacting a tumor cell with an effective amount of an antibody against ubiquitin. Preferably, this antibody is MEL-14, [e.g., MEL-14-F(ab')$_2$], antibody 14372 or antibody 10C2-2.

The methods of the invention represent a new and improved carcinogenesis model for in vitro studies of tumor cell migration and in vivo studies using animals with transplanted with marker-gene modified bone marrow, for example, eGFP transgeneics. Additional features and advantages of the invention will be forthcoming from the following detailed description of certain specific embodiments when read in conjunction with the accompanying drawings.

BRIEF DESCRIPTION OF THE DRAWINGS

FIG. 1 is a schematic illustration of malignant transformation mediated by fusion between bone marrow derived stem cells and "altered" tissue cells.

DESCRIPTION OF THE PREFERRED EMBODIMENTS

As used herein, a "metastasis" means the spread of cancer from one part of the body to another. A tumor formed by cells that have spread is called a "metastatic tumor" or a "metastasis."

The term "malignant" means cancerous, i.e., abnormal cells that divide without control and that can invade nearby tissues and spread through the bloodstream and lymphatic system to other parts of the body.

The terms "altered cell" or "genetically altered cell" are defined here as any cells with genetic or epigenetic changes sufficient to skew the normal differentiation pathway of a bone marrow derived stem cell after fusion with a BMDSC.

"Altered" cells include so-called "initiated" (pre-malignant) cells in the multiple-step carcinogenesis model.

The term "fusion cell" means a cell formed by the fusion of an altered cell and a bone marrow derived stem cell.

The origin of malignancy is still controversial, especially for carcinomas, which comprise more than 90% of human malignancy. The model of carcinogenesis put forward by the inventors focuses on the developmental origin of highly malignant carcinomas. The key event in this model is a fusion step between bone marrow-derived stem cells (BMDSC) and "altered" tissue cells (FIG. 1). Purified BMDSC populations are obtained by removing all bone marrow derived cells that expressed a differentiated cell surface markers using commercially available columns. The lineage negative cells that passes through the columns can be further enriched for stem cells by positively selecting for CD34 positive, CD133 positive and SCA-1 positive cells. This works for both mouse and human BMDSC. The invention relates in part to the recognition that the fusion between "altered" tissue cells with BMDSC may result in malignant transformation of the hybrid cells. Thus, so-called "initiated" cells in multiple step carcinogenesis model and benign tumor cells can be given the ability to migrate.

Upon fusion, the normal differentiation pathway of BMDSC could be disrupted due to the existing genetic or epigenetic disorder of the "altered" tissue cells. Genetic disorders could be gene mutations, translocations, deletions, or amplifications as proposed by the gene mutation hypothesis. Epigenetic disorders could be any change beyond the DNA sequences that result in dysregulation of cell growth and function, such as DNA methylation, chromatin modification, or altered cellular signaling. Fusion could give rise to daughter cells with the phenotype of both the altered cells and BMDSC. In other words, the daughter cells could acquire the capability of self-renewal, tissue invasion and migration from BMDSC, thereby turning into malignant cells. Moreover, the fusion process, subsequent mitosis and loss of individual copies of chromosomes, will result in aneuploidy. Aneuploidy could become the driving force of genomic instability and cancer progression. According to the inventor's model, a single fusion event could have the same transforming (from benign to malignant) effect as that of multiple events involved in the process of classical multistage carcinogenesis.

Based on the inventor's model, most of the malignant phenotype of cancer such as invasion and metastasis would come from the BMDSC. Fusion is a natural and relatively frequent event during the development and maintenance of multicellular organisms. In comparing the relative probability of gene mutation and the stem cell fusion, one can view the development of a normal cell to full malignancy as an evolutionary process. Any pathway that replaces multiple rare events with a frequent event would result in such pathway to be overwhelmingly preferred in evolution.

BMDSC are highly plastic. Many studies demonstrate that bone marrow not only contains hematopoietic stem cells (HSC), but also contains mesenchymal stem cells (MSC), endothelial cell progenitors, and stem cells of epithelial tissues that can differentiate into epithelial cells of liver, lung, skin, and gastrointestinal tract. These BMDSC migrate to nonhematopoietic tissues and may play a role in maintenance and repair of damaged tissue. There are, as summarized in Table 1, striking similarities between BMDSC and metastatic cancer cells in terms of their biological activities, as well as the molecular basis of these activities.

TABLE 1

Similarity between bone marrow-derived stem cells and metastatic cancer cells.

| Bone marrow-derived Stem cells | Metastatic cancer cells |
| --- | --- |
| Self-renewal | "Immortality" |
| Growth in suspension | Anchorage-independent growth |
| Multilineage differentiation | Give rise to heterogenic cancer cells |
| Migration | Invasion, metastasis |
| Extravasation | Extravasation |
| Surface markers, c-kit, CD34 and CD133 | Some cancer cells express c-kit, CD34 and CD133 |
| Chemokine receptors, such as CXCR4 | CXCR4 expressed in metastatic tumor |
| Sensitive to radiation | Poorly differentiated cancer more sensitive to radiotherapy |
| Express telomerase | Telomere maintenance |
| Partial immune privilege | Immune escape |
| Wnt and Hedgehog signal activity | Wnt and Hedgehog signal activity |
| Mediate angiogenesis | Mediate angiogenesis |

BMDSC and metastatic cancer cells are capable of self-renewal, migration, and tissue invasion. Certain cancer cells express purported stem cell markers. For example, c-kit is strongly expressed in serous ovarian carcinoma, testicular carcinoma, malignant melanoma, and small cell lung carcinoma. CD34 is expressed in dermatofibrosarcoma, epitheloid sarcoma, and solitary fibrous tumors. In addition, all types of cancer cells acquire telomere maintenance capability, similar to stem cells, which are telomerase positive. BMDSC express particular chemokine receptors and reach their destination by chemokine-ligand interactions.

Interestingly, the same chemokine-ligand pairs are involved in homing of BMDSC and malignant cell metastasis. A well-known phenomenon is that poorly differentiated cancer is usually highly metastatic but more sensitive to radiotherapy. This phenomenon has not been fully addressed in the literature, but bears remarkable resemblance to BMDSC that are highly sensitive to radiation. Indeed, this sensitivity to radiation is the basis of clinical myeloablation. Taken together, cancer cells may acquire these characteristics from BMDSC. In fact, recent data has shown that bone marrow derived cells can give rise to gastric cancer in mice with chronic Helicobacter infections. In addition, there is a report that human skin carcinomas derived from donor cells were observed in a kidney transplant recipient.

The inventors have proposed in the past that a fusion event between BMDSC and "altered" cells give rise to cancer cell migration. As mentioned above, fusion is a fundamental phenomenon in the life of many organisms. Intracellular vesicle fusion is essential for basic cellular function. Enveloped viruses deliver viral capsids into the cytosol through membrane fusion. From yeast to humans, life begins with fusion. Cell-cell fusion is a part of normal biological processes during the development of muscle, bone and placenta. As early as 1911, it has been proposed that malignancy could be a consequence of hybridization between leukocytes and somatic cells. Studies also showed that oncogenic transformation occurred when mammalian somatic cells took up co-cultured sperm, and/or via the experimentally-induced penetration of spermatozoa in situ. A long standing hypothesis was that hybridization of tumor cells with lymphocytes results in metastatic cells. However, prior to the invention, no one is know to have described or suggested that malignant transformation is a result of fusion between a BMDSC and "altered" pre-malignant tissue cells.

Stem cells are capable of adopting the phenotype of other cells by spontaneous cell fusion. Several studies have shown that BMDSC fuse with a variety of target cells. Using a method based on Cre/lox recombination to detect cell fusion events, Alvarez-Dolado et al. (*Nature* 425, 968-973 [2003]) demonstrated that bone-marrow-derived cells fuse in vivo with liver hepatocytes, Purkinje neurons in the brain and cardiac muscle in the heart, resulting in the formation of multinucleated cells. Through serial transplantation of bone-marrow-derived hepatocytes, Wang et al. (*Nature* 422, 897-901[2003]) demonstrate that cell fusion is the principal source of bone-marrow-derived hepatocytes. Cytogenetic analysis of hepatocytes transplanted from female donor mice into male recipients demonstrated diploid to diploid fusion (80, XXXY) and diploid to tetraploid fusion (120, XXXXYY) karyotypes. In theory, fusion can occur multiple times between normal, pre-malignant and malignant cells; however, the invention specifically involves fusion between an "altered" pre-malignant tissue cell and BMDSC as a crucial step in carcinogenesis. There may be multiple fusions with the BMDSC, thereby leading to at least a tetraploid karyotype after fusion takes place.

After fusion with altered tissue cells, the normal self-renewal and differentiation of stem cells is thought to be disrupted by the abnormal signal derived from the altered cells. In contrast to other stem cell models of carcinogenesis, which propose that stem cells accumulate mutations and become transformed, the invention is consistent with the studies that show that stem cells are less tolerant to DNA damage than differentiated cells. Stem cells should be more sensitive to DNA damage in order to maintain the multipotent differentiation potential. There is no doubt that BMDSC are more sensitive to radiation than mature cells. This fact is the basis of clinical myeloablation. There is also the observation that tissue stem cells are more sensitive to killing by DNA-damaging agents. Apoptosis levels of intestinal crypt stem cells are markedly elevated by exposure to radiation or cytotoxic agents. Therefore, it is more likely that tissue cells, rather than stem cells, accumulate genetic and epigenetic disorders. After fusion with BMDSC, the daughter cells are transformed and give rise to malignant tumors.

Chromosomal abnormalities have been identified as one of the distinctive pathological features of cancer for more than 100 years. Aneuploidy has been observed in nearly all solid human cancers. In addition, clinical data suggest that the degree of aneuploidy is correlated with the severity of the diseases. An aneuploidy hypothesis of cancer emphasized the importance of aneuploidy in carcinogenesis, but the mechanism underlying aneuploidy remains unclear. In the stem cell fusion model of carcinogenesis described here, aneuploidy is an inevitable consequence of cell fusion resulting in loss of individual chromosome copies. In an earlier direct application of the proposed stem cell fusion model of carcinogenesis, studies demonstrated hyperchromasia in prostate cancer cells could be a consequence of presumptive fusion of injected spermatozoa with normal prostatic epithelial cells. Moreover, certain human precancerous lesions have shown increased frequency of tetraploid cells, such as Barrett's esophagus, ulcerative colitis, and HPV-positive atypical cervical squamous cells. Analysis of DNA ploidy demonstrates that the majority of aneuploid human prostate cancers are tetraploid. This evidence suggests that the aneuploidy of cancer originates from a tetraploidation event (i.e., fusion).

The association between chronic tissue injury, inflammation and cancer has long been observed. There are many elegant studies and reviews of the molecular and cellular mechanisms underlying this association. The inventors' interpretation of the relationship between tissue repair and carcinogenesis is as follows. Chronic tissue injury, inflammation, and subsequent tissue repair exhaust the regenerative capacity of local tissue stem cells. The local inflammatory microenvironment then favors homing of BMDSC and their involvement in tissue repair. BMDSC occasionally fuse with "altered" tissue cells and give rise to malignant transformation.

Tissues that normally undergo rapid renewal are expected to experience an increased cancer incidence, as a high turnover rate should result in local tissue stem cell exhaustion and infiltration of BMDSC. Indeed, epithelium in the skin, the lungs, and the gastrointestinal tract, which are continuously exposed to environmental insult and constantly in a state of renewal, are the tissues with a high proportion of cancers. The increased engraftment of bone marrow derived keratinocytes during wound healing has been demonstrated in sex-mismatched bone marrow transplanted mice, though the same study ruled out the presence of fusion between bone marrow-derived cells and skin epithelial cells in acute injury. Helicobacter infection is a major attributable factor in the development of gastric cancer. Chronic tissue damage and ongoing tissue repair cause an imbalance between epithelial cell proliferation and apoptosis in the stomach. Indeed, it recently was reported that bone marrow-derived cells are the origin of gastric cancer in Helicobacter-infected mice.

Aging is one of the greatest risk factors of cancer. Analysis of the age distribution of cancer resulted in the early multistage theory of carcinogenesis. Later, the gene mutation hypothesis assumed that the age distribution of cancer reflected the time required to accumulate sufficient multiple mutations for cancer development. However, an alternative explanation could be that mechanisms responsible for aging also impact stem cell function. Oxidative damage and cell senescence could enhance the frequency of improper cell-cell fusion and increase the incidence of malignancy. For instance, senescent cells compromise tissue renewal or repair, secrete factors that can alter the tissue microenvironment, and in turn could alter the activity of stem cells. In addition, stem cells themselves are also a direct target for aging-related damage. It has been demonstrated that hair graying is caused by defective self-maintenance of melanocyte stem cells. Gut epithelial stem cells have been shown to suffer important functional impairment with aging. Senescence and a functional failure of HSCs can create conditions that are permissive to leukemia development. Therefore, the chronological kinetics of carcinogenesis may reflect the cell-cell interactions during the course of aging.

Other conditions may promote cell-cell fusion and consequently increase the incidence of cancer, including tissue remodeling and virus infection. The high incidence of breast and ovarian cancer in women, and hepatocellular carcinoma following chronic hepatitis may be examples where tissue remodeling promotes malignant transformation. Epstein-Barr virus (EBV) has been shown to be associated with a wide range of cancers including Burkitt's lymphoma, non-Hodgkin's lymphoma, Hodgkin's disease, Nasopharyngeal carcinoma, gastric adenocarcinoma and breast cancer. Earlier studies have shown that EBV induces cell-cell fusion, especially by virus isolated from tumors. In concert with these data, the inventor's stem cell fusion model of carcinogenesis could explain why EBV infection associates with so many cancers.

The stem cell fusion model of carcinogenesis presented here is readily testable. Thus, several experiments that have been performed by the inventors. Fusion between benign tumor cells and BMDSC has been performed in vitro. After fusion, the morphology and capability for metastasis and invasion are determined in vitro and in vivo. Evidence of also fusion could be shown by thorough examination of the spontaneous solid tumors developed in mice receiving sex-mismatched bone marrow or transgenic bone marrow. However, because the redundant sex chromosome is often lost in the daughter cells when fusion happens, the widely used technology such as fluorescence in situ hybridization (FISH) for detecting the sex chromosome, might not be appropriate. Indeed, a considerable number of malignant tumors that develop in normal females become sex-chromatin negative, suggesting the loss of the redundant second X chromosome. Methods to detect the presence of transduced DNA species, or donor-derived mitochondria DNA might be suitable. Finally, a retrospective study could be done by examination of samples collected from previous bone marrow recipients who later developed carcinomas. Techniques, such as detection of the presence of the donor-derived mitochondrial DNA rather than FISH detecting sex chromosome, may be more informative.

The stem cell fusion model of cancer, especially carcinoma, has significant implications for cancer research and drug development, as well as for the therapeutic application of stem cells. Malignant cells might be susceptible to therapies that induce differentiation. Differentiation could switch off self-renewal activity and decrease the capability of malignant cells to metastasize and invade tissues. In fact, several differentiation-inducing agents, such as retinoic acid or peroxisome proliferators-activated receptor-gamma (PPARγ) agonists, have been used for the successful treatment of acute myeloid leukemia or liposarcoma, respectively. Introduction of a differentiation signal into malignant cells through gene transfer might be a novel viable approach for cancer therapy. In addition, metastatic cells might have a homing pattern similar to BMDSC; therefore, approaches to block BMDSC homing could be used to inhibit cancer metastasis. In agreement with this, a recent study has demonstrated that silencing of the chemokine receptor CXCR4 through RNA interference blocks breast cancer metastasis in mice. Cancer is difficult to control because its genetics are so chaotic. However, the BMDSC derived malignant characteristics of the cancer cells could present a conserved target for design of new therapies.

Thus, cancer metastasis would use the same conserved molecular mechanisms as the BMDSC and their progeny that include neutrophils, lymphocytes, and other leukocytes. Therefore, the inventors have examined whether antibodies to ubiquitin, which can block neutrophils, lymphocytes, and other leukocytes' motility and extravasation in vivo, will block cancer cell's motility and extravasation and therefore block metastasis. Furthermore, determining the presence of the of BMDSC/altered cell fusions in tumors could alert the attention of researchers to a possible unintended consequence of stem cell-based therapy (i.e., improper administration of stem cells might actually increase the incidence of malignancy).

Chronic tissue damage and subsequent repair exhaust tissue stem cells and recruit BMDSC, therefore increasing the chance for the fusion of BMDSC with tissue cells. Other factors, such as aging, viral infection and tissue remodeling, also enhance the incidence of cell fusion. Importantly, one fusion step could render multiple "malignant" characteristics to transform an "altered" cell without requiring multiple mutations.

While hundreds of studies involving fusion of tumor cells and non-tumor cells and the effect on tumorigenicity have been performed, no studies on the fusion of bone marrow-derived stem cells and tumor cells were found in the scientific literature prior to the invention.

Hence, in a first embodiment of the invention, a method for modeling cancer cell migration includes the steps of: (a) providing a bone marrow derived stem cell; (b) providing a genetically altered cell; (c) fusing the bone marrow derived stem cell with the genetically altered cell, thereby creating a fused cell; and (d) measuring an indicator of migration for the fused cell. Both BMDSC and genetically altered cells are readily available from commercial and academic tissue culture and live sources. Likewise, cell fusion is routinely practiced such that there are many protocols available (see, for example, the hybridoma protocols at protocol-online.org.). Measuring an indicator of migration for the fused cell (and it progeny) can be done through an in vitro "scratch assay" (e.g., Lal A, Glazer C A, Martinson H M, et al. *Cancer Res* 2002, 62:3335-3340) or through in vivo animal studies (e.g., injection of tumor cells including one or more fused cells and monitoring metastasis as described in the examples below).

The invention further involves method for screening an effect of a biological or chemical agent on tumor cell migration either in vitro or in vivo. The method includes providing a fused cell derived from a fusion of a bone marrow derived stem cell with a genetically altered cell; contacting the fused cell with a biological or chemical agent, and determining whether tumor cell migration is promoted, inhibited, or unchanged. Conserved proteins would be an especially good target for screening the effects of agents on migration.

Ubiquitin(ub) is the most conserved protein found in nature. Among its sequence of 76 amino acids, there is complete homology between species as evolutionarily divergent as insects, trout, and human. Ubiquitin makes up part of the outer surface domains of several other membrane receptors. In the case of Lymphocyte homing receptors(LHR), the presence of ub is closely correlated to LHR's function in facilitating the binding and migration of Lymphocytes through lymph nodes. All of the receptors that have been shown to be linked to ub have also been known to mediate cellular mobility. A possible explanation of these observations is that ub is involved in mediating cellular mobility through the extracellular matrix. This potential function of ub has important implications in the studies of many eukaryotic processes such as cell differentiation, parasite infection, tumor invasion and tumor cell metastasis.

Hence, for example, the biological or chemical agent is an antibody against ubiquitin, such as MEL-14 (CD62L) (available through Abcam Plc., Zymed Laboratories, et al.; see abcam.com for 21 different antibodies to ubiquitin). The cells contacted by this antibody have been subjected to a scratch assay or used in animal experiments to determine the effect of the antibody on cell migration as described below.

In another embodiment of the invention, a method for inhibiting tumor cell migration is described to include contacting a tumor cell with an effective amount of an antibody against ubiquitin. Preferably, this embodiment includes the step of confirming the presence of a fused cell among the tumor cells prior to contacting the tumor cells with the antibody so that such inhibition can be targeted to tumors with greater malignant potential.

One may determine if the tumor cell sample contains a cell with at least tetraploid DNA and at least one cell-surface marker specific to a bone marrow derived stem cell. Such surface cell markers include c-kit, CD34 and CD133 and chemokine receptors, such as CXCR4. One also may include utilizing Cre/lox recombination to detect a fusion of a bone marrow derived stem cell and a non-stem cell.

NON-LIMITING EXAMPLES

The experimental techniques to be used in these investigations are well-established and widely accepted.

The goal of this first study is to test a previously proposed hypothesis for carcinogenesis, in which the interaction of bone marrow derived stem cells and transformed cells can alter tumor progression. Two types of experiments can be performed. In the first set of experiments, cells derived from mouse bone marrow are isolated from mice which transgenically express eGFP and combined with transiently transfected transformed human or mouse cells labeled with Clontech's red fluorescent protein under conditions which facilitate the formation of hybrid cells. These hybrid cells will then be injected into a strain of mice appropriate for the cell line being tested.

Alteration of primary or metastatic tumor growth is monitored as a function of time. Two basic questions addressed by this study are whether tumor progression is modulated by the fusion of bone marrow-derived stem cells with tumor cells in various stages of transformation, and whether treatment of human or mouse xenografts with antibodies to receptors will alter the metastatic phenotypes of the xenograft tumors. A representative receptor which serves as a model to test these hypotheses is CXCR4, which is expressed by metastatic tumor cells.

Well-established xenograft models of tumor growth and progression in athymic nude, Balb/c or SCID mice must be used so that the host immune response to the administration of transformed mouse (308, 308 10Gy5, or 4T1) and human (DU145 or PC-3 M) cell lines, well-established model systems for breast, skin, and prostate cancer, will be minimal. Subcutaneous inoculation or tail vein injection is used to administer mouse cell lines into athymic nude mice. The human cell lines are administered to SCID mice. An aliquot containing cell lines, singly or in combination, are injected on day 0 and tumor growth is followed for a maximum of 40 days. Mice are then be sacrificed, tissues removed, and tumor volume and relative levels of lung metastases quantitated.

Experiment 1

Group A: 8 Transgenic Mice

Heterozygous transgenic eGFP mice [C57BL/6-TgN (ACTbEGFP)1Osb] (Jackson Laboratory) are used as a source of GFP labeled bone marrow cells. GFP mice are identified by expression of green fluorescence under UV light. 2- to 4-month old female heterozygotes are used as the donors for the BMT. Donor's gender is different from that of the recipient host.

Bone marrow derived cells are obtained from heterozygous GFP mice by flushing the femur and tibia with Hanks' balanced solution. To generate somatic cell hybrids, $10^6$ bone marrow-derived cells and 106 tumor cells are plated on 60 mm dishes 24 hours before treatment with polyethylene glycol (PEG). 5 grams of PEG with a molecular weight of 3000-3700 is prepared by autoclaving for 5 minutes at 121 degrees C. The autoclaved PEG is then combined with 5 ml of 2× sterile serum-free medium, pre-warmed to 37 C to prepare a 50% solution. One ml of the 50% PEG solution per dish is then added slowly to the co-cultured cells, and the cells are incubated for 1 minute at 37 degrees.

One ml of the serum-free medium is then added, and incubation continued for an additional 1 minute. Two ml of the medium is then added, and incubation continued for 2 minutes. Four ml of serum-free medium and incubation continued for 4 minutes. Medium containing serum is then added to each plate, and incubation continued for 48 hours at 37 C. After two days, each dish is passaged with trypsin and replated onto four 100 mm plates for selection. Cells expressing markers characteristic of both types of co-cultured cells are selected and grown to 90% confluence and used in subsequent experiments.

Experiment 2

Altered Tumorigenicity and Progression of Mouse and Human Benign Tumor Cells

Mice are inoculated with GFP-labeled bone marrow cells, singly or in combination with transformed benign human or mouse cells.

Group A: 72 mice. Strains: Athymic nude mice for 308 cells; SCID for DU145 or PC-3 M tumors (Pain category D). Total mice needed: (4 mice/treatment) (6 treatments) (3 experiments)=72 mice.

Mice are inoculated with GFP-labeled bone marrow (BM)-derived cells and/or with transformed benign human or mouse cells. Tumor inoculations are performed on mice anesthetized with isofluorane in a bell jar. The mice are placed in the jar which contains isofluorane treated cotton balls inside a polypropylene centrifuge tube. During the procedure the mice are monitored by observing respiratory rate, movement, muscle relaxation, and lack of directed movement. After inoculation, mice are returned to their cages and monitored until they regain normal consciousness.

100 ul of PBS containing $5 \times 10^5$ cells is administered to each mouse. Athymic nude mice receive 308 cells, BM cells, or a PEG-treated mixture of BM cells and 308 cells. SCID mice receive DU145 cells, BM cells, or a PEG-treated mixture of BM cells and DU145 cells. Inoculations are administered subcutaneously or by tail vein injection. For those mice receiving tail vein infections, the mice are confined in a restraint box. After disinfection of the tail with alcohol, 2% xylacaine is applied as a topical anesthetic. No more than 200 ul of solution is injected into each mouse, using a 25-30 gauge needle. If the injections cause necrosis, the tails are sprayed with ethyl chloride, dipped in betadine, and removed with sterile scissors just above the necrotic area. The tail then is cauterized with silver nitrate to stop bleeding.

Tumor growth is monitored by caliper measurement o tumor dimensions twice weekly, and calculation of volume using the formula: Volume_+½(length)(lengtth$^2$) Animals is sacrificed at 2, 3, and 4 weeks to monitor for the extent of metastasis and the volume of tumor achieved.

Animals are sacrificed by carbon dioxide asphyxiation in an airtight chamber in order to harvest tumors and organs. This is a routinely used procedure for euthanasia of mice that minimizes their suffering and is recommended by the AVMA Panel on Euthanasia.

Summary Outline of Procedure

1. Administer mixture of benign transformed cells and stem cells to establish 308 and DU145 xenografts by subcutaneous or tail vein injection.
2. Treatment groups for each method of injection—(6): 308 cells; BM cells; PEG-treated mixture of BM cells+308 cells; DU145; BM cells, PEG treated DU145 and BM cell mixture.
3. Primary tumors and organs with metastases which develop will be removed after termination of the mice by $CO_2$ asphyxiation.
4. Submit tumor samples for histopathological analysis to detect alterations in progression or the ability to metastasize associated with a fusion event. The histopathological analysis should include comparison of tumor growth with time, relative numbers and sizes of metastases, histological characterization of the tumor.

Experiment 3

Inhibition of Tumorigenicity or Progression

Mice are inoculated with metastatic transformed human (PC3-M) or mouse (308 10Gy5 or 4T1) cells, and with inhibitors of the CRCX4 receptor. Total mice needed: (4 mice/treatment) (3 treatments) (3 timepoints of administration) (3 experiments)=108 mice.

Tumor inoculations are performed on mice anesthetized with isofluorane in a bell jar. The mice are placed in the jar which contains isofluorane treated cotton balls inside a polypropylene centrifuge tube. During the procedure the mice are monitored by observing respiratory rate, movement, muscle relaxation, and lack of directed movement. After inoculation, mice are returned to their cages and monitored until they regain normal consciousness.

100 ul of PBS containing $10^4$ 4T1 cells is administered injected into a mammary fat pad of 4 Balb/c mice. The athymic nude mice receive 100 ul of PBS containing $1\times10^6$ 308 10Gy5 cells. The SCID mice receive 100 ul of PBS containing $1\times10^6$ PC-3M cells. The experiment is performed with administration of the antibody to the CRCX4 receptor before, concurrently, and after inoculation of tumor cells. 4T1 cells are injected into Balb/c mammary fat pads. 308 10Gy5 are injected into tail veins of nude mice, and PC-3 M cells are injected into the tail veins of SCID mice. The mice receiving tail vein injections are confined in a restraint box during the injection. After disinfection of the tail with alcohol and application of 2% xylacaine as a topical anesthetic, no more than 200 ul of solution is injected into each mouse, using a 25-30 gauge needle. If the injections cause necrosis, the tails is sprayed with ethyl chloride, dipped in betadine, and removed with sterile scissors just above the necrotic area. The tail then is cauterized with silver nitrate to stop bleeding.

Tumor growth is monitored by caliper measurement of tumor dimensions twice weekly, and calculation of volume using the formula: Volume=½ (length)(length$^2$) Animals are sacrificed at 10, 15, and 20 days to monitor for lung metastases and tumor volume.

Animals are monitored for pre- or post-inoculated with a potential inhibitor of metastasis and assayed for alterations in tumor cell apoptosis, differentiation, inhibition of metastasis.

Primary tumors and metastases which develop in the host mice are removed after termination of the mice by $CO_2$ asphyxiation.

Tissue samples are submitted for histopathological analysis to detect alterations in progression or metastasis associated with the treatment. The histopathological analysis should include comparison of tumor growth with time, relative numbers and sizes of metastases, histological characterization of the tumor tissue.

In Vitro Cancer Cell/Fused Cell Migration Inhibition Assay:

Cells: Two metastatic cancer cell lines were used to test the ability of ubiquitin antibodies to inhibit cell motility. PC-3M is a human prostate carcinoma cell line. 4T1 is a mouse mammary carcinoma cell line. Both were maintained and in DMEM medium supplemented with 10% FBS and Glutamax 1 (DMEM medium).

Antibodies: Three ubiquitin antibodies were used. 14372 is a polyclonal antibody to ubiquitin. 10C2-2 and Mel-14 are both monoclonal antibodies to ubiquitin.

Procedure (1): A 6-well plate containing a sterile coverslip in each well was seeded with $1\times10^6$ cells/well in DMEM medium, and incubated overnight at 37° C. and 5% $CO_2$, in a humidified incubator (standard conditions).

The next day, the confluent monolayer on the coverslip was scratched once with a pipette tip. The medium was aspirated and the wells were rinsed with 1 mL of DMEM medium. Each cell line was treated with three different concentrations of each antibody: 5 µg/mL/$10^6$ cells, 25 µg/mL/$10^6$ cells and 100 µg/mL/$10^6$ cells. The plates were incubated for 11 hours with the cells. Control cells were treated with DPBS.

The coverslips were evaluated after incubation for closure of the scratches as a result of cell migration. The coverslips were then fixed and stained with 1:1 methanol:acetone for 5 minutes at −20° C. and then rinsed with DPBS. Coverslips were mounted on glass slides. Images were captured with Metacam software using a workstation composed of an Nikon TE2000 microscope at 4× magnification.

In Vivo Cancer Cell/Fused Cell Metastasis Inhibition Assay:

Cells: A metastatic mouse mammary carcinoma cell line, 4T1, was used to test the ability of a ubiquitin antibody to inhibit metastasis. The cells were maintained in DMEM medium under the culture conditions described in the previous protocol.

Antibodies: The monoclonal ubiquitin antibody, Mel-14, was used.

Procedure: 4T1 cells were transiently transfected with an expression vector for the enhanced green florescence protein (EGFP). Cells were harvested 48 hours after transfection and incubated with either ubiquitin antibody, Mel-14, or a control antibody, Rat IgG2A, at the concentrations of 180 µg per $10^6$ cells in DPBS for one hour. After incubation, 250,000 cells were injected into the tail vein of SCID mice in a total volume of 50 µL. One week later, the mice were sacrificed and their lungs were removed and fixed in 4% formalin. Examination for the presence of metastatic colonies was performed on whole flattened lungs with a Nikon Eclipse 600 microscope at 10× magnification. The presence of EGFP positive cells in the lung indicated that metastasis has occurred.

Results:

TABLE 2

Degree of inhibition of migration of PC3M cells in vitro by ubiquitin antibodies at different concentrations.

| antibodies | Conc. | | |
|---|---|---|---|
|  | 5 µg/ml/$10^6$ | 25 µg/ml/$10^6$ | 100 µg/ml/$10^6$ |
| 14372 | ++++ | ++++ | ++++ |
| 10C2-2 | ++++ | ++++ | ++++ |
| Mel-14 | ++++ | ++++ | ++++ |
| DPBS only | − | − | − |

++++ = complete inhibition;
− = no inhibition

TABLE 3

Degree of inhibition of migration of 4T1 cells in vitro by ubiquitin antibodies at different concentrations.

| antibodies | Conc. | | |
|---|---|---|---|
|  | 5 µg/ml/million | 25 µg/ml/million | 100 µg/ml/million |
| 14372 | ++++ | ++++ | ++++ |
| 10C2-2 | ++++ | ++++ | ++++ |
| Mel-14 | ++++ | ++++ | ++++ |
| DPBS only | − | − | − |

++++ = complete inhibition;
− = no inhibition

TABLE 4

Degree of inhibition of in vivo metastasis
of 4T1 cells by ubiquitin antibody, Mel-14.

| antibodies | Conc.<br>180 µg/10$^6$ |
|---|---|
| Mel-14 | ++++ |
| control antibody | − |

++++ = complete inhibition;
− = no inhibition

Reference:
1. Auerbach R, Lewis R, Shinners B, Kubal L, Akhtar N. "Angiogenesis Assays: A Critical Overview" Clinical Chemistry 49 (1), 1 Jan. 2003:32-40.

As seen in the tables above, antibodies against ubiquitin inhibited migration of tumor cells.

Therapeutic Methods

The methods of this invention may be used to inhibit tumor migration in a subject. A vertebrate subject, preferably a mammal, more preferably a human, is administered an amount of the compound effective to inhibit tumor cell migration. The compound or pharmaceutically acceptable salt thereof is preferably administered in the form of a pharmaceutical composition.

Doses of the compounds preferably include pharmaceutical dosage units comprising an effective amount of the antibody or other agent. By an effective amount is meant an amount sufficient to achieve a steady state concentration in vivo which results in a measurable reduction in any relevant parameter of disease.

Monoclonal antibodies are now routinely used for therapy by infusion directly into the patient. The antibody can be lyophilized and stored until reconstitution with either water or saline. A dose of 4 mg/kg body weight is a typical and safe human dosage for antibody-based therapies. For example, this is an effective dose of the breast cancer antibody therapy Herceptin. Thus, in one embodiment of the invention, a human patient is dosed at 4 mg of a anti-ubiquitin antibody per kg body weight that is given intravenously.

The amount of active compound to be administered depends on the precise biological or chemical agent, the disease or condition, the route of administration, the health and weight of the recipient, the existence of other concurrent treatment, if any, the frequency of treatment, the nature of the effect desired, for example, inhibition of tumor metastasis, and the judgment of the skilled practitioner.

The foregoing compositions and treatment methods are useful for inhibiting cell migration (e.g., invasion or metastasis) in a subject having any disease or condition associated with undesired cell invasion, proliferation, metastasis.

Various modifications are possible within the meaning and range of equivalence of the appended claims.

We claim:

1. A method for inhibiting mammalian tumor cell migration, comprising contacting a tumor cell with a composition comprising, in an amount effective to inhibit mammalian tumor cell migration, an antibody against ubiquitin in a pharmaceutically acceptable carrier.

2. A method for inhibiting human tumor cell migration, comprising contacting a tumor cell with a composition comprising, in an amount effective to inhibit human tumor cell migration, an antibody against ubiquitin in a pharmaceutically acceptable carrier.

3. The method of claim 1, wherein said effective amount is about 4 mg of anti-ubiquitin antibody per kilogram of body weight.

4. The method of claim 1 wherein said effective amount is between about 5 µg/ml/million cells to 100 µg/ml/million cells in-vitro.

5. The method of claim 2, wherein said effective amount is about 4 mg of anti-ubiquitin antibody per kilogram of body weight.

6. The method of claim 2, wherein said effective amount is between about 5 µg/ml/million cells to 100 µg/ml/million cells in-vitro.

* * * * *